US011195059B2

(12) United States Patent
Takeshima

(10) Patent No.: US 11,195,059 B2
(45) Date of Patent: Dec. 7, 2021

(54) SIGNAL DATA PROCESSING APPARATUS

(71) Applicant: Canon Medical Systems Corporation, Otawara (JP)

(72) Inventor: Hidenori Takeshima, Kawasaki (JP)

(73) Assignee: Canon Medical Systems Corporation, Otawara (JP)

( * ) Notice: Subject to any disclaimer, the term of this patent is extended or adjusted under 35 U.S.C. 154(b) by 96 days.

(21) Appl. No.: 16/554,770

(22) Filed: Aug. 29, 2019

(65) Prior Publication Data

US 2020/0082205 A1 Mar. 12, 2020

(30) Foreign Application Priority Data

Sep. 6, 2018 (JP) .............................. JP2018-166717

(51) Int. Cl.
*G06K 9/62* (2006.01)
*G16H 30/40* (2018.01)
*G06N 3/08* (2006.01)

(52) U.S. Cl.
CPC ........... *G06K 9/627* (2013.01); *G06K 9/6215* (2013.01); *G06N 3/08* (2013.01); *G16H 30/40* (2018.01)

(58) Field of Classification Search
CPC .............................. G06K 9/627; G06K 9/6215
See application file for complete search history.

(56) References Cited

U.S. PATENT DOCUMENTS

| 9,307,496 | B2 * | 4/2016 | Saitoh | H04W 52/248 |
| 2017/0004603 | A1 * | 1/2017 | Irie | H04N 5/23229 |
| 2018/0025112 | A1 | 1/2018 | Takeda | |
| 2019/0336033 | A1 | 11/2019 | Takeshima | |

FOREIGN PATENT DOCUMENTS

| JP | 10-40363 A | 2/1998 |
| JP | 11-31214 A | 2/1999 |
| JP | 2018-14059 A | 1/2018 |
| JP | 2019-93126 A | 6/2019 |

OTHER PUBLICATIONS

Schlemper, J. et al., "A deep Cascade of Convolutional Neural Networks for MR Image Reconstruction," arXiv:1703.00555[cs.CV]. https://arxiv.org/abs/1703.0055, Mar. 1, 2017, 12 pages.

Zhu, B. et al., "Deep Learning MR reconstruction with Automated Transform by Manifold Approximation (AUTOMAP) in real-world acquisitions with imperfect training: simulation and in-vivo experiments," ISMRM Workshop on Machine Learning, Poster 46, Mar. 2018, 1 page.

Zhu, B. et al., "Image reconstruction by domain-transform manifold learning," Nature, vol. 555, Mar. 22, 2018, pp. 487-492.

* cited by examiner

*Primary Examiner* — Tuan H Nguyen

(74) *Attorney, Agent, or Firm* — Oblon, McClelland, Maier & Neustadt, L.L.P.

(57) ABSTRACT

According to one embodiment, a signal data processing apparatus includes processing circuitry. The processing circuitry obtains first signal data of a plurality of frames that are in time series, selects a processing target frame among the frames and a reference frame that is similar to the processing target frame, inputs the first signal data of the processing target frame and the first signal data of the reference frame to the machine learning model, and outputs second signal data in which a deficient part of the first signal data corresponding to the processing target frame is reduced.

11 Claims, 6 Drawing Sheets

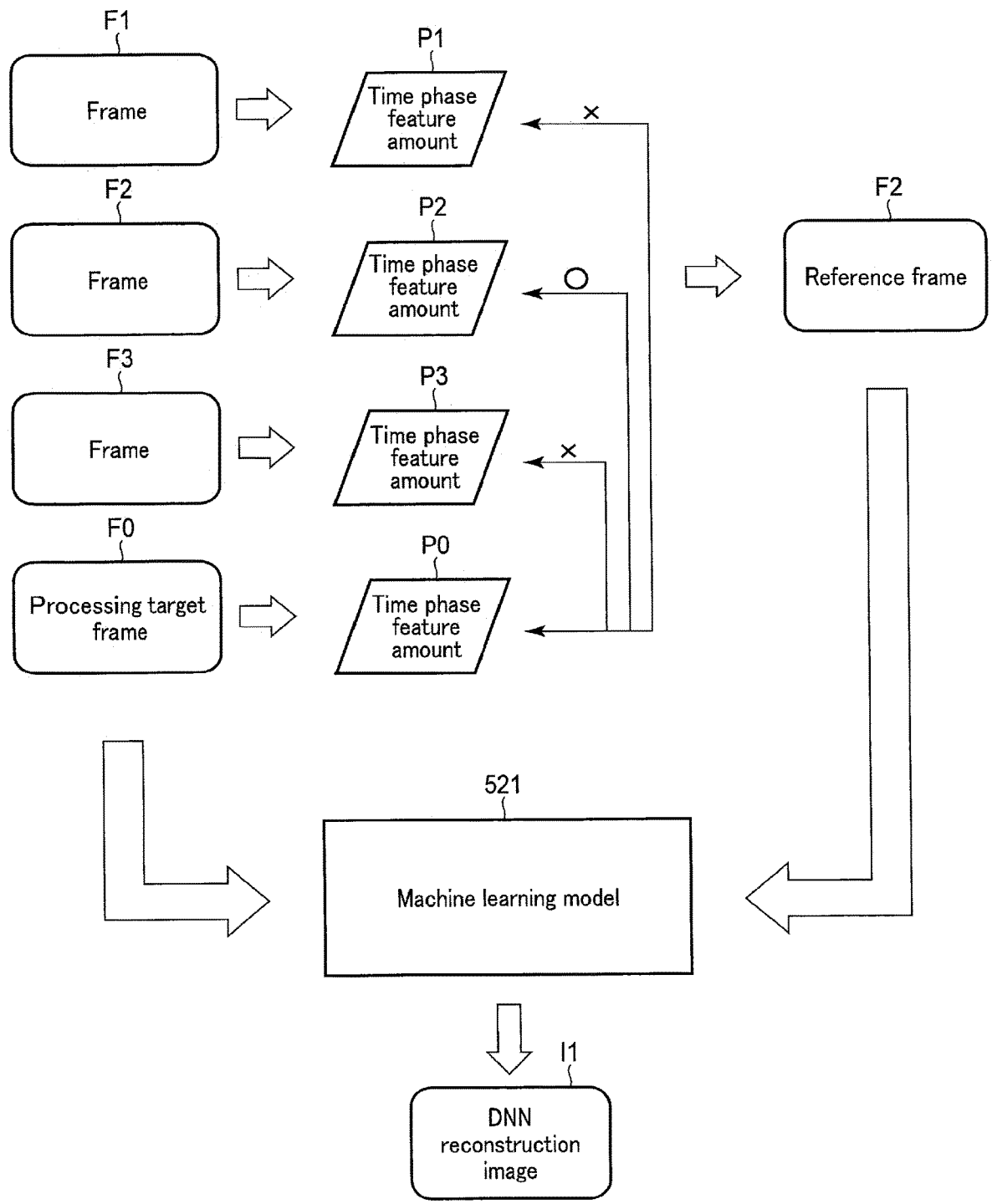
F I G. 4

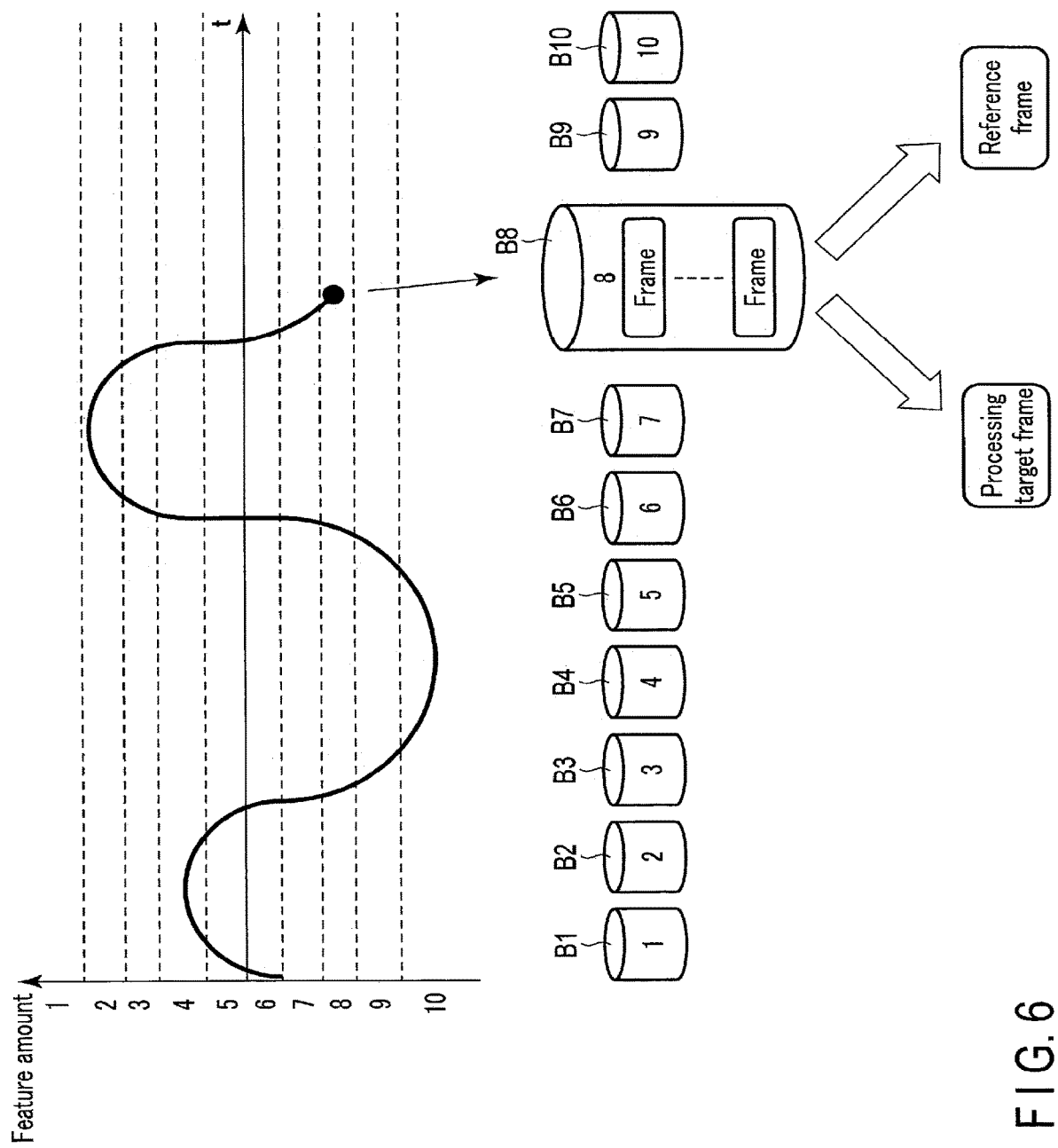
F I G. 6

SIGNAL DATA PROCESSING APPARATUS

CROSS-REFERENCE TO RELATED APPLICATIONS

This application is based upon and claims the benefit of priority from the Japanese Patent Application No. 2018-166717, filed Sep. 6, 2018 the entire contents of which are incorporated herein by reference.

FIELD

Embodiments described herein relate generally to a signal data processing apparatus.

BACKGROUND

In machine learning using medical signal data such as a medical image and its raw data, there is a method to apply a deep neural network (DNN) learned from an amount of training data in order to restore an original signal from a partly deficient medical signal. For example, in magnetic resonance imaging (MRI), there is a DNN which has a processing target image and a reference image input, and outputs an image in which a deficient part of the processing target image is restored. However, since the reference image is an image that is imaged at a different time from the processing target image, in some cases, the form of a subject may differ between the time of imaging the reference image and the time of imaging the processing target image. In this case, the degree to which the reference image correlates with the processing target image may be low, and the image quality of the output image may deteriorate.

BRIEF DESCRIPTION OF THE DRAWINGS

FIG. 4 is a drawing schematically showing a process of FIG. 3.

FIG. 6 is a drawing schematically showing a selection of a processing target frame and a reference frame according to modified example 2.

DETAILED DESCRIPTION

In general, according to one embodiment, a signal data processing apparatus comprises processing circuitry. The processing circuitry obtains first signal data of a plurality of frames that are in time series, selects a processing target frame among the frames and a reference frame that is similar to the processing target frame, inputs the first signal data of the processing target frame and the first signal data of the reference frame to the machine learning model, and outputs second signal data in which a deficient part of the first signal data corresponding to the processing target frame is reduced.

The signal data processing apparatus according to the present embodiment will be explained with reference to the accompanying drawings.

The signal data processing apparatus according to the present embodiment is an apparatus in which processing circuitry for processing signal data of a plurality of frames that are in time series is mounted. The signal data processing apparatus is realized by, for example, a computer mounted on a medical image diagnostic apparatus. The medical image diagnostic apparatus that acquires signal data may be a single modality apparatus such as a magnetic resonance imaging apparatus (MRI apparatus), an X-ray computed tomography apparatus (CT apparatus), an X-ray diagnostic apparatus, a positron emission tomography (PET) apparatus, a single photon emission CT apparatus (SPECT apparatus), and a ultrasound diagnostic apparatus, and also may be a combined modality apparatus such as a PET/CT apparatus, a SPECT/CT apparatus, a PET/MRI apparatus, and a SPECT/MRI apparatus. As other examples, the signal data processing apparatus may be a computer communicably connected to the medical image diagnostic apparatus via a cable, a network, or the like, or may be a computer independent of the medical image diagnostic apparatus. Hereinafter, the signal data processing apparatus is assumed to be mounted on the magnetic resonance imaging apparatus.

Figure 1:
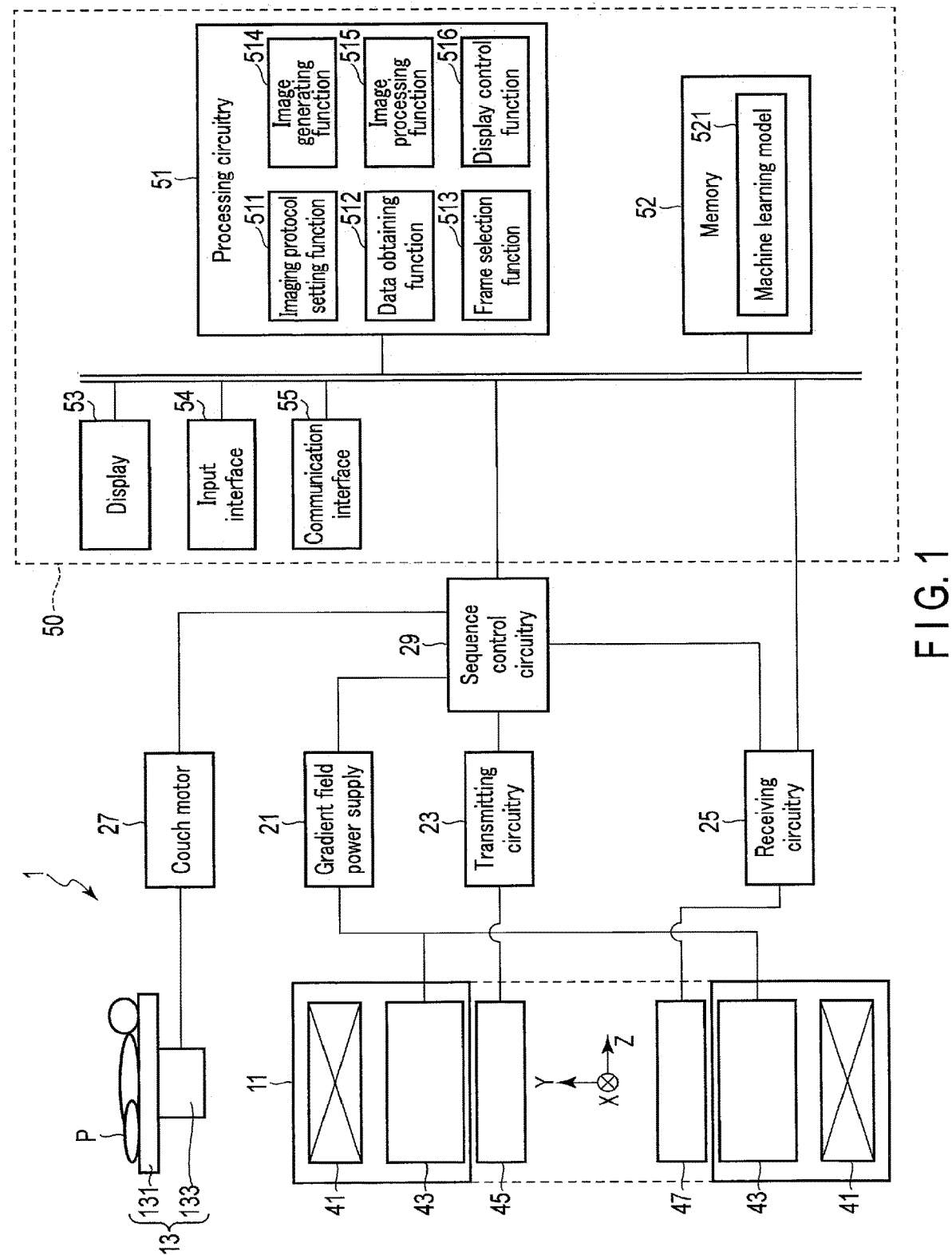
FIG. 1 is a view showing a configuration of a magnetic resonance imaging apparatus on which a signal data processing apparatus according to the present embodiment is mounted.

FIG. 1 is a view showing a configuration of a magnetic resonance imaging apparatus 1 on which a signal data processing apparatus 50 according to the present embodiment is mounted. As shown in FIG. 1, the magnetic resonance imaging apparatus 1 includes a gantry 11, a couch 13, a gradient field power supply 21, transmitting circuitry 23, receiving circuitry 25, a couch motor 27, sequence control circuitry 29, and a signal data processing apparatus 50.

The gantry 11 includes a static field magnet 41 and a gradient field coil 43. The static field magnet 41 and the gradient field coil 43 are accommodated in the housing of the gantry 11. The housing of the gantry 11 is formed with a bore having a hollow shape. A transmitting coil 45 and a receiving coil 47 are disposed in the bore of the gantry 11.

The static field magnet 41 has a hollow substantially cylindrical shape and generates a static magnetic field inside a substantially cylindrical interior. Examples of the static field magnet 41 used include a permanent magnet, a superconducting magnet or a normal conducting magnet. Here, a central axis of the static field magnet 41 is defined as a Z axis, an axis vertically perpendicular to the Z axis is defined as a Y axis, and an axis horizontally perpendicular to the Z axis is defined as an X axis. The X axis, the Y axis and the Z axis constitute an orthogonal three-dimensional coordinate system.

The gradient field coil 43 is a coil unit attached to the inside of the static field magnet 41 and formed in a hollow substantially cylindrical shape. The gradient field coil 43 receives supply of a current from the gradient field power supply 21 to generate a gradient field. More specifically, the gradient field coil 43 has three coils corresponding to the X axis, the Y axis, and the Z axis orthogonal to each other. The three coils form a gradient field in which the magnetic field strength changes along the X axis, the Y axis, and the Z axis respectively. The gradient fields respectively along the X axis, the Y axis, and the Z axis are combined to form slice selection gradient fields Gs, phase encoding gradient fields Gp, and frequency encoding gradient fields Gr that are orthogonal to each other in arbitrary directions. The slice selection gradient fields Gs are arbitrarily used to determine the imaging cross section. The phase encoding gradient fields Gp are used to change the phase of the MR signal according to a spatial position. The frequency encoding gradient fields Gr are used to change the frequency of the MR signal according to the spatial position. It should be noted that in the following description, it is assumed that the direction of gradient of the slice selection gradient fields Gs corresponds to the Z axis, the direction of gradient of the phase encoding gradient fields Gp corresponds to the Y axis, and the direction of gradient of the frequency encoding gradient fields Gr corresponds to the X axis.

The gradient field power supply 21 supplies a current to the gradient field coil 43 in accordance with a sequence control signal from the sequence control circuitry 29. The gradient field power supply 21 supplies a current to the gradient field coil 43 and causes the gradient field coil 43 to generate a gradient field along each of the X axis, Y axis, and Z axis. The gradient field is superimposed on the static magnetic field formed by the static field magnet 41 and applied to a subject P.

The transmitting coil 45 is disposed, for example, inside the gradient field coil 43, and receives supply of a current from the transmitting circuitry 23 to generate a high frequency magnetic field pulse (hereinafter referred to as an RF magnetic field pulse).

The transmitting circuitry 23 supplies a current to the transmitting coil 45 in order to apply an RF magnetic field pulse for exciting a target proton in the subject P to the subject P via the transmitting coil 45. The RF magnetic field pulse oscillates at a resonance frequency specific to the target proton to excite the target proton. A magnetic resonance signal (hereinafter referred to as an MR signal) is generated from the excited target proton and detected by the receiving coil 47. The transmitting coil 45 is, for example, a whole-body coil (WB coil). The whole-body coil may be used as a transmitting and receiving coil.

The receiving coil 47 receives the MR signal emitted from the target proton present in the subject P under an action of the RF magnetic field pulse. The receiving coil 47 has a plurality of receiving coil elements capable of receiving the MR signal. The received MR signal is supplied to the receiving circuitry 25 via wire or wireless. Although not shown in FIG. 1, the receiving coil 47 has a plurality of receiving channels implemented in parallel. The receiving channels each include receiving coil elements that receive the MR signal, an amplifier that amplifies the MR signal, and the like. The MR signal is output for each receiving channel. The total number of the receiving channels and the total number of the receiving coil elements may be the same, or the total number of the receiving channels may be larger or smaller than the total number of the receiving coil elements.

The receiving circuitry 25 receives the MR signal generated from the excited target proton via the receiving coil 47. The receiving circuitry 25 processes the received MR signal to generate a digital MR signal. The digital MR signal can be expressed in k-space defined by a spatial frequency. Therefore, hereinafter, the digital MR signal is referred to as k-space data. The k-space data is a type of raw data to be provided for image reconstruction. The k-space data is supplied to the signal data processing apparatus 50 via wire or wireless.

It should be noted that the transmitting coil 45 and the receiving coil 47 described above are merely examples. Instead of the transmitting coil 45 and the receiving coil 47, a transmitting and receiving coil having a transmitting function and a receiving function may be used. Also, the transmitting coil 45, the receiving coil 47, and the transmitting and receiving coil may be combined.

The couch 13 is installed adjacent to the gantry 11. The couch 13 has a table top 131 and a base 133. The subject P is placed on the table top 131. The base 133 slidably supports the table top 131 respectively along the X axis, the Y axis, and the Z axis. The couch motor 27 is accommodated in the base 133. The couch motor 27 moves the table top 131 under the control of the sequence control circuitry 29. The couch motor 27 may, for example, include any motor such as a servo motor or a stepping motor.

The sequence control circuitry 29 has a processor of a central processing unit (CPU) or a micro processing unit (MPU) and a memory such as a read only memory (ROM) or a random access memory (RAM) as hardware resources. The sequence control circuitry 29 synchronously controls the gradient field power supply 21, the transmitting circuitry 23, and the receiving circuitry 25 based on the imaging protocol determined by an imaging protocol setting function 511 of the processing circuitry 51, executes a pulse sequence corresponding to the imaging protocol to perform MR imaging on the subject P, and acquires the k-space data on the subject P. The k-space data is a type of signal data according to the present embodiment.

As shown in FIG. 1, the signal data processing apparatus 50 is a computer having processing circuitry 51, a memory 52, a display 53, an input interface 54, and a communication interface 55.

The processing circuitry 51 includes, as hardware resources, a processor such as a CPU, a graphics processing unit (GPU), and an MPU, and a memory such as a ROM and a RAM. The processing circuitry 51 functions as the core of the magnetic resonance imaging apparatus 1. For example, by executing various programs, the processing circuitry 51 realizes the imaging protocol setting function 511, a data obtaining function 512, a frame selection function 513, an image generating function 514, an image processing function 515, and a display control function 516.

In the imaging protocol setting function 511, the processing circuitry 51 sets an imaging protocol relating to MR imaging of a target by user instruction via the input interface 54 or automatically. The imaging protocol is a set of various imaging parameters related to one MR imaging. Examples of imaging parameters include various imaging parameters set directly or indirectly for performing MR imaging such as imaging time, type of k-space filling method, type of pulse sequence, TR, TE, and the like.

In the data obtaining function 512, the processing circuitry 51 obtains signal data of a plurality of frames that are in time series regarding the subject P. The signal data according to the present embodiment may be any data that can be acquired or generated by the magnetic resonance imaging apparatus. For example, the signal data is a collective term of k-space data or hybrid data based on the k-space data, and data of an MR image based on the k-space data. The hybrid data is data that is generated by applying Fourier transform with respect to the k-space data regarding an arbitrary direction. Obtaining signal data includes acquisition of signal data via the receiving circuitry 25 in MR imaging performed under the control of the processing circuitry 51, selection of signal data of an arbitrary frame from among the signal data of a plurality of frames, and reception, transfer, or transmission, etc. of signal data from other apparatuses. The processing circuitry 51 also obtains output data (hereinafter referred to as external measuring equipment data) from external measuring equipment such as an electrocardiograph, respiratory motion measuring equipment (respiration sensor), and the like. The external measuring equipment data is associated with the signal data per frame and managed.

In the frame selection function 513, the processing circuitry 51 selects a processing target frame from among a plurality of frames. Furthermore, the processing circuitry 51 selects a reference frame that satisfies a predetermined criterion regarding similarity of the signal data with respect to the processing target frame from among a plurality of frames. The similarity of signal data may be determined directly by the matching rate of signal data between the processing target frame and the reference frame or calculated, or may be estimated indirectly by the matching rate of a body motion phase of the processing target frame and the reference frame. The body motion phase indicates a phase regarding an approximate cyclic motion of a human body, such as a heart phase or a respiration phase.

In the image generating function 514, the processing circuitry 51 inputs the signal data of the processing target frame and the signal data of the reference frame to the machine learning model 521, and outputs signal data of the processing target frame. The machine learning model 521 is generated by the signal data processing apparatus 50 or other computers, etc. in advance, and is stored in the memory 52.

Figure 2:
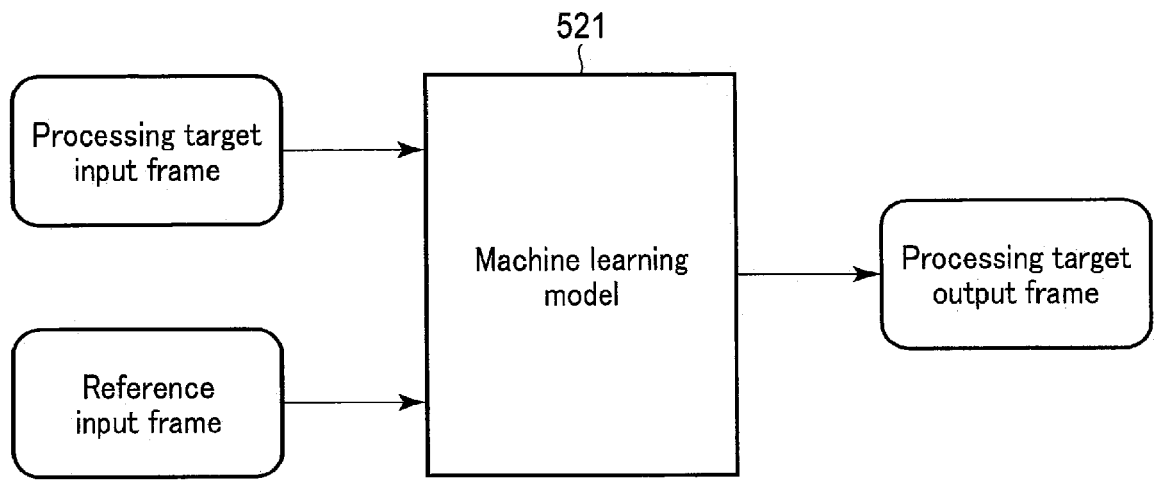
FIG. 2 is a drawing showing an input/output relationship of a machine learning model used by an image generating function of FIG. 1.

FIG. 2 is a diagram showing an input/output relationship of the machine learning model 521. As shown in FIG. 2, the machine learning model 521 is a machine learning model in which parameters are learned to receive input of the signal data of the processing target frame (processing target input frame) and the signal data of the reference frame (reference input frame), and to output the signal data of the processing target frame (processing target output frame). The machine learning model 521 is a parameterized synthesis function defined by a combination of a plurality of adjustable functions and parameters (weighting matrices or biases). The machine learning model 521 is realized by a deep network model (DNN: Deep Neural Network) having, for example, an input layer, an intermediate layer, and an output layer. Hereinafter, the reconstruction processing using the machine learning model 521 will be referred to as DNN reconstruction.

In the image generating function 514, the processing circuitry 51 performs the DNN reconstruction using the machine learning model 521 on the signal data of the processing target frame and the signal data of the reference frame to generate an MR image (hereinafter referred to as a DNN reconstruction image). There are less signal deficiencies in the DNN reconstruction image than in the MR image generated by performing Fourier transform on the k-space data of the processing target frame. In other words, image quality tends to improve. The signal deficiency according to the present embodiment is a concept including any difference between actual signal data and desired signal data regarding a subject. For example, signal deficiency includes signal deterioration due to noise caused by various causes, signal loss due to reduction in the number of samplings of signal data by under sampling of k-space data, etc., and information deficiency due to conversion from a continuous value to a discrete value generated in the process of A/D conversion, etc.

The types of input data and output data depend on the machine learning model 521. For example, a certain machine learning model 521 may input k-space data as the input data, and output k-space data in which signal deficiencies are reduced more compared to the input k-space data as the output data. In this case, the processing circuitry 51 generates the DNN reconstruction image by performing Fourier transform on the output k-space data. Other machine learning models 521 may input an MR image as the input data, and output a DNN reconstruction image in which signal deficiencies are reduced more compared to the input MR image as the output data. In this case, the processing circuitry 51 generates an MR image by performing Fourier transform on the k-space data obtained by the data obtaining function 512, and inputs the generated MR image to the machine learning model 521. Other machine learning models 521 may input k-space data as the input data, and generate, as the output data, a DNN reconstruction image in which signal deficiencies are reduced more compared to the MR image generated by performing Fourier transform on the input k-space data. Hereinafter, the machine learning model 521 will input k-space data as the input data, and generate a DNN reconstruction image as the output data.

In the image processing function 515, the processing circuitry 51 performs various types of image processing on the DNN reconstruction image. For example, the processing circuitry 51 performs image processing such as volume rendering, surface rendering, pixel value projection processing, Multi-Planer Reconstruction (MPR) processing, Curved MPR (CPR) processing, and the like.

In the display control function 516, the processing circuitry 51 displays various types of information on the display 53. For example, the processing circuitry 51 displays the DNN reconstruction image, an imaging protocol setting screen, and the like on the display 53.

The memory 52 is a storage apparatus such as a hard disk drive (HDD), a solid state drive (SSD), an integrated circuitry storage apparatus or the like that stores various information. The memory 52 may be a drive apparatus or the like that reads and writes various information from and to a portable storage medium such as a CD-ROM drive, a DVD drive, a flash memory, and the like. For example, the memory 52 stores signal data, a control program, the machine learning model 521, and the like.

The display 53 displays various types of information. For example, the display 53 displays a DNN reconstruction image generated by the image generating function 514, a setting screen of an imaging protocol, and the like. Examples of appropriate displays 53 that can be used include a CRT display, a liquid crystal display, an organic EL display, an LED display, a plasma display, or any other display known in the art.

The input interface 54 includes an input apparatus that receives various commands from the user. Examples of the input apparatus that can be used include a keyboard, a mouse, various switches, a touch screen, a touch pad, and the like. It should be noted that the input apparatus is not limited to those having physical operation parts such as the mouse and the keyboard. For example, the examples of input interface 54 also include electrical signal processing circuitry that receives an electrical signal corresponding to an input operation from an external input apparatus provided separately from the magnetic resonance imaging apparatus 1, and outputs the received electrical signal to various types of circuitry.

The communication interface 55 is an interface connecting the magnetic resonance imaging apparatus 1 with a workstation, a picture archiving and communication system (PACS), a hospital information system (HIS), a radiology information system (RIS), and the like via a local area network (LAN) or the like. The network IF transmits and receives various information to and from the connected workstation, PACS, HIS and RIS.

It should be noted that the above configuration is merely an example, and the present invention is not limited thereto. For example, the sequence control circuitry 29 may be incorporated into the signal data processing apparatus 50. Also, the sequence control circuitry 29 and the processing circuitry 51 may be mounted on the same substrate. The sequence control circuitry 29, the gradient field power supply 21, the transmitting circuitry 23 and the receiving circuitry 25 may be mounted on a single control apparatus different from the signal data processing apparatus 50 or may be distributed and mounted on a plurality of apparatuses.

Hereinafter, an operation example of the magnetic resonance imaging apparatus 1 and the signal data processing apparatus 50 according to the present embodiment will be explained.

Figure 3:
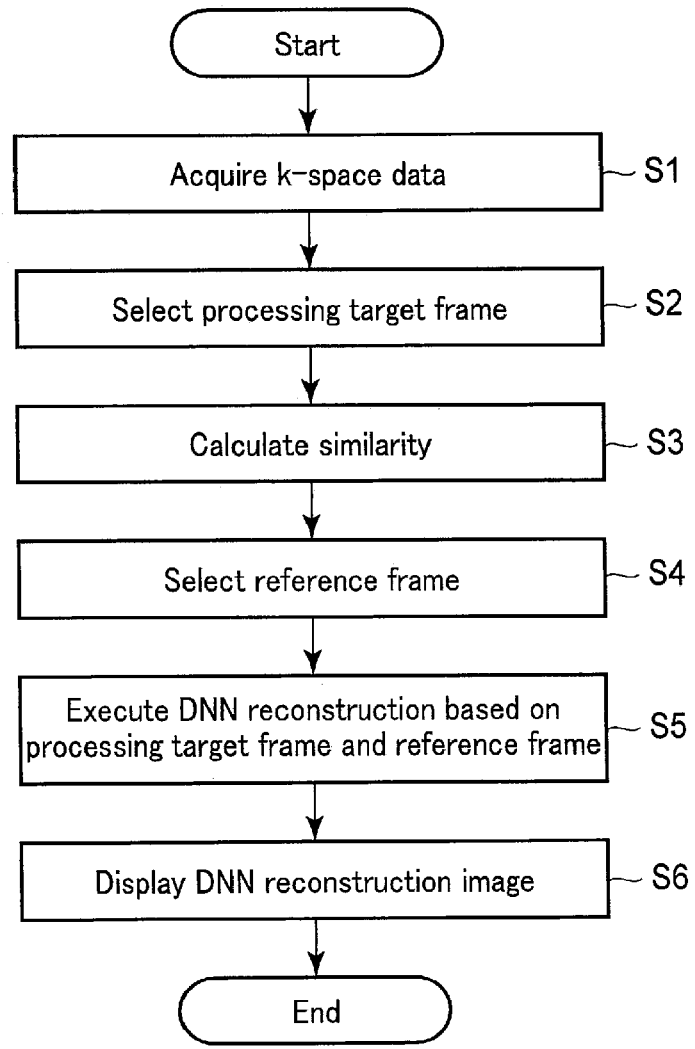
FIG. 3 is a drawing showing a typical flow of MR imaging by processing circuitry of FIG. 1.

FIG. 3 is a drawing showing a typical flow of MR imaging by the processing circuitry 51. FIG. 4 is a drawing schematically showing a process of FIG. 3. The process shown in FIG. 3 starts after the sequence control circuitry 29 performs MR imaging on the subject P. Dynamic imaging (dynamic MRI) that acquires k-space data of a plurality of frames for the heart, the chest, and the abdomen, etc. of the subject P is suitable for the MR imaging performed in FIG. 3.

As shown in FIG. 3, by the data obtaining function 512, the processing circuitry 51 obtains k-space data of a plurality of frames in time series via the receiving circuitry 25 (step S1). Step S1 is performed in real time when performing MR imaging. That is, each time the k-space data of one frame is obtained, steps S2 to S6 of the subsequent stages are performed.

When step S2 is performed, by the frame selection function 513, the processing circuitry 51 selects a processing target frame F0 from among the plurality of frames obtained in step S1 (step S3). The selection criterion of the processing target frame F0 can be set as appropriate. For example, an earliest frame in which the DNN reconstruction image is not generated may be selected, or a latest frame may be selected among a plurality of frames. Furthermore, the frame may be selected by a user via the input interface 54.

When step S3 is performed, by the frame selection function 513, the processing circuitry 51 calculates the similarity between the processing target frame F0 and the frames other than the processing target frame (step S4). Similarity is an indicator that indicates the similarity of signal data between the processing target frame F0 and the other frames Fn (n is an integer). Similarity is, for example, defined by an error between a time phase feature amount P0 of the processing target frame F0 and a time phase feature amount Pn of other frames Fn (n is an integer). A time phase feature amount is an indicator that depends on the form of an object (subject P) drawn on an MR image of the frame. As the time feature amount, for example, the MR image of the frame is used. In this case, the processing circuitry 51 generates the MR image by performing Fourier transform on the k-space data of the processing target frame F0, and sets the generated MR image as the time phase feature amount P0. Similarly, the processing circuitry 51 generates the MR image by performing Fourier transform on the k-space data of the other frames Fn, and sets the generated MR image as the time phase feature amount Pn. As the similarity, the processing circuitry 51 calculates an error based on data collation between the MR image P0 of the processing target frame F0 and the MR image Pn of each of the other frames. For example, a difference value for each pixel between the MR image P0 and the MR image Pn is calculated, and a total value of the difference values of all of the pixels is calculated as the similarity.

In the case of using an MR image of the frame as the time phase feature amount, an MR image generated by performing Fourier transform on all regions of the k-space data may be used, or an MR image generated by performing Fourier transform on a limited part of the k-space data (for example, low area) may be used. Furthermore, in the case of a method of acquiring a part of the k-space data in each frame as in, for example, a pulse sequence using an auto calibration signal (ACS), a PROPELLER method, or a Stack-of-Stars scanning method, the k-space data itself, or spectrum data (or an MR image) generated by applying Fourier transform on the k-space data may be used.

As the time phase feature amount, output data (hereinafter referred to as measuring equipment data) from external measuring equipment such as an electrocardiograph, respiratory motion measuring equipment, and the like may be used. As the respiratory motion measuring equipment, for example, a respiratory abdominal belt (respiratory belt), mechanical measuring equipment, optical measuring equipment, an optical camera, and the like are used. The processing circuitry 51 sets the measuring equipment data of the processing target frame F0 as the time phase feature amount P0, and sets the measuring equipment data of the other frames Fn as the time phase feature amount Pn. The processing circuitry 51 calculates an error based on data collation between the measuring equipment data P0 of the processing target frame F0 and the measuring equipment data Pn of each of the other frames as the similarity. For example, the difference value between the measuring equipment data of the processing target frame F0 and the measuring equipment data of the other frames Fn is calculated, and such difference value is calculated as the similarity. Furthermore, as the time phase feature amount, the k-space data or the hybrid data may be used.

As the time phase feature amount, a signal value that is obtained by a navigation echo applied in the data acquisition of the frame may also be used. Specifically, from among the signal values obtained by the navigation echo applied in the data acquisition of the frame, the signal value of any time may be used. A signal value that corresponds to a time, or a plurality of signal values that correspond to each of a plurality of times may be used. As the plurality of signal values, a plurality of signal values themselves respectively corresponding to the plurality of times included in a certain time range may be used, or a waveform of a plurality of signal values may be used. Furthermore, statistics of an average value or an intermediate value of a plurality of signal values may be used as the time phase feature amount.

When step S3 is performed, the processing circuitry 51 selects a reference frame from among the frames other than the processing target frame by the frame selection function 513 (step S4). More specifically, the processing circuitry 51 selects the reference frame in accordance with the similarity regarding each of the other frames Fn with respect to the calculated processing target frame. In the case where the similarity is the difference value of the time phase feature amount, for example, the difference value of each of the other frames Fn is compared with the threshold value, and the frame below the threshold value is selected as the reference frame. In the case where there are a plurality of frames that are below the threshold value, the frame with the smallest difference value may be selected as the reference frame, or the frame with the closest time phase may be selected as the reference frame, or the reference frame may be selected by other criteria. For example, in the case of FIG. 4, frame F2 that has the highest similarity with the time phase feature amount P0 of the processing target frame F0 is selected as the reference frame.

When step S4 is performed, by the image generating function 514, the processing circuitry 51 executes DNN reconstruction based on the processing target frame and the reference frame, and generates a DNN reconstruction image regarding the processing target frame (step S5). In step S5, the processing circuitry 51 applies the k-space data of the processing target frame F0 and the k-space data of the reference frame F2 to the machine learning model 521, and generates a DNN reconstruction image I1 regarding the processing target frame F0.

The input of the machine learning model 521 is not limited to the signal data of the processing target frame and the signal data of the reference frame. For example, the machine learning model 521 may also be a DNN in which parameters are learned so that the signal data of the processing target frame, the signal data of the reference frame, and the similarity of the reference frame with respect to the processing target frame are input, and de-noised signal data of the processing target frame is output. The input form of the similarity is not limited in particular; however, for example, it is preferable to prepare matrices in the same size as the signal data, and to use data in which a value of the similarity is assigned to all of the elements of the matrices. In this manner, by using the similarity also for the input, the accuracy of the output signal data can be expected to further improve.

Furthermore, the machine learning model 521 may also be a DNN in which parameters are learned so that the signal data of the processing target frame, the signal data of the reference frame, and acquisition time differences between the processing target frame and the reference frame are input, and de-noised signal data of the processing target frame is output. The acquisition time difference is defined by the difference between the acquisition time of the k-space data of the processing target frame and the acquisition time of the k-space data of the reference frame. The input form of the acquisition time difference is not limited in particular; however, for example, it is preferable to prepare matrices in the same size as the signal data, and to use data in which a value of the acquisition time difference is assigned to all of the elements of the matrices. In this manner, by using the acquisition time difference also for the input, the accuracy of the output signal data can be expected to further improve.

When step S5 is performed, the processing circuitry 51 displays the DNN reconstruction image on the display 53 by the display control function 516 (step S6).

Hereby, the explanation on the typical flow of the MR imaging by the processing circuitry 51 is ended.

In the same manner as the above, steps S2 to S6 are performed for all of the frames in which the k-space data is acquired in the dynamic imaging. In this manner, the DNN reconstruction image of a plurality of frames can be displayed in a moving image.

As mentioned above, the signal data processing apparatus 50 includes at least the processing circuitry 51. The processing circuitry 51 realizes the data obtaining function 512, the frame selection function 513, and the image generating function 514. By the data obtaining function 512, the processing circuitry 51 obtains first signal data of a plurality of frames that are in time series regarding a subject. By the frame selection function 513, the processing circuitry 51 selects a processing target frame from among a plurality of frames and a reference frame that satisfies a predetermined criterion regarding similarity with respect to the processing target frame. By the image generating function 514, the processing circuitry 51 inputs first signal data of the processing target frame and first signal data of the reference frame to the machine learning model 521, and outputs second signal data of the processing target frame.

According to the present embodiment, since other frames with signal data that is most similar to that of the processing target frame can be selected as the reference frame, the image quality of the DNN reconstruction image of the processing target frame can be improved.

In the above explanation, the reference frame to be input to the machine learning model 521 is one frame. However, the present embodiment is not limited thereto. The reference frame to be input to the machine learning model 521 may be two or more frames. For example, in the case where the reference frames are three frames, the three frames in the top three similarities should be selected as the reference frames.

MODIFIED EXAMPLE 1

In the above explanation, the reference frame is selected from among all of the frames for which data acquisition was performed by the dynamic imaging. However, the present embodiment is not limited thereto.

Figure 5:
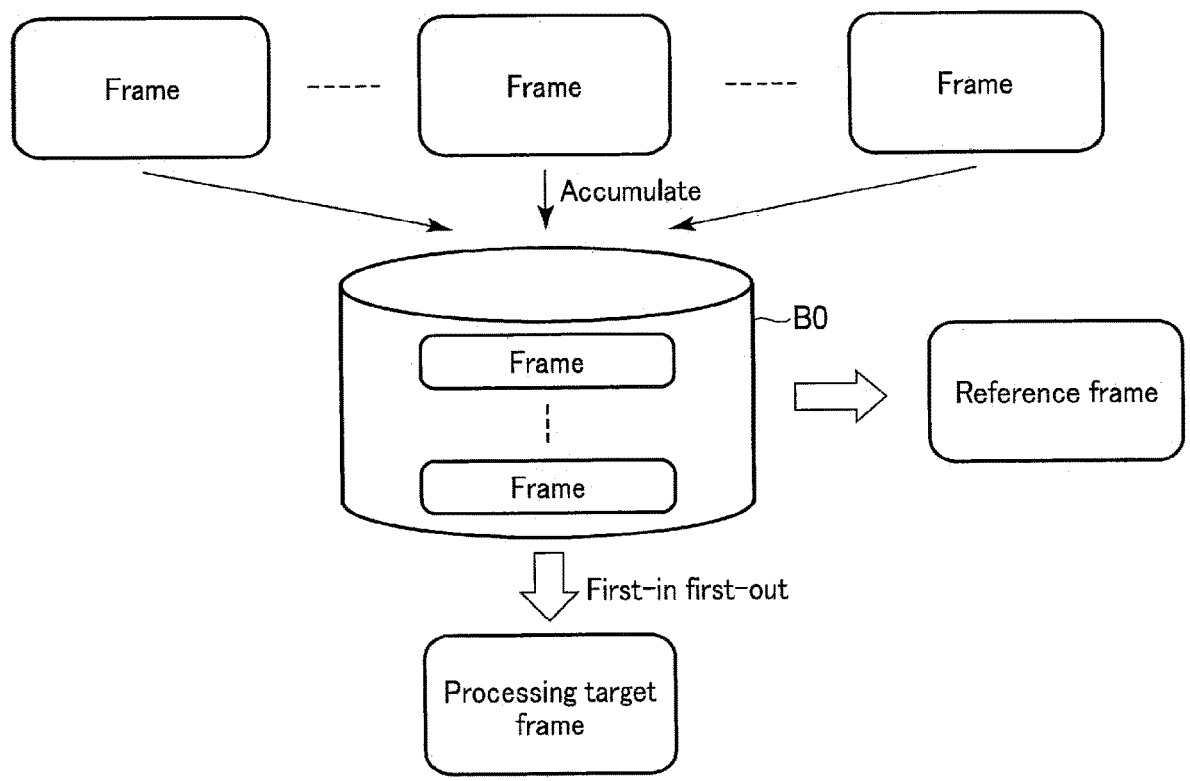
FIG. 5 is a drawing schematically showing a selection between a processing target frame and a reference frame according to modified example 1.

FIG. 5 is a drawing schematically showing a selection of a processing target frame and a reference frame according to modified example 1. As shown in FIG. 5, upon dynamic imaging, k-space data is acquired regarding a plurality of frames. The k-space data of the plurality of frames acquired in modified example 1 is accumulated in real time in a first-in first-out buffer (FIFO buffer) B0. The FIFO buffer B0 is assumed to be able to accumulate k-space data of N frames (N is an integer) at maximum. In this case, the k-space data of the latest N frames are accumulated in the FIFO buffer B0. For example, processing circuitry 51 selects a frame taken out (first-in first-out) from the FIFO buffer B0 as a processing target frame, and selects a reference frame from among the latest N frames accumulated in the FIFO buffer B0. By limiting selection candidates of the reference frame to the latest N frames accumulated in the FIFO buffer B0, the reference frame can be selected from among frames close to the processing target frame in terms of time. The FIFO buffer B0 may be provided on a memory 52, or may be provided on the processing circuitry 51.

The processing target frame may also be selected from among the latest N frames accumulated in the FIFO buffer B0.

MODIFIED EXAMPLE 2

In the above embodiment, the DNN reconstruction is performed after ending the dynamic imaging. However, the DNN reconstruction may be performed when performing the dynamic imaging.

FIG. 6 is a drawing schematically showing a selection of a processing target frame and a reference frame according to modified example 2. As shown in FIG. 6, a time phase feature amount is classified into a plurality of classes in advance in accordance with a value. For example, during predetermined seconds after starting the dynamic imaging, k-space data continues to accumulate in a buffer. Predetermined seconds are defined as a time in which data can be acquired to an extent that allows estimating a value the time phase feature amount may take. For example, in the case of abdominal imaging, the time is set to approximately two breaths, for example, approximately 10 seconds. The time phase feature amount shown in FIG. 6 is output data of a respiration sensor (external measuring equipment data).

After the lapse of predetermined seconds, processing circuitry 51 identifies or calculates the time phase feature amount of each frame, and estimates a range the time phase feature amount may take. For example, a minimum value min and a maximum value max are identified from among the identified or calculated time phase feature amounts, and a range from min-α to max+α obtained by adding a predetermined margin a to the minimum value min and the maximum value max is set as the range that may be taken. By dividing the range that may be taken equally by a predetermined number, the processing circuitry 51 classifies the time phase feature amount into a predetermined number of classes. The predetermined number may be set to any number. In the case of FIG. 6, the time phase feature amount is classified into 10 classes.

A queue (a queue, a FIFO buffer) is provided for each class. In each queue, the k-space data of a corresponding class is accumulated in units of frames. For example, in the case of FIG. 6, there are 10 classes. Therefore, 10 FIFO buffers Bn (n is an integer from 1 to 10) are provided. The processing circuitry 51 stores the k-space data of each frame in a corresponding FIFO buffer Bn. The processing circuitry 51 selects a reference frame from among the frames stored in order from the first frame in the FIFO buffer Bn, and executes DNN reconstruction. The FIFO buffer Bn may be provided on a memory 52, or may be provided on the processing circuitry 51.

For example, in the case of FIG. 6, since the time phase feature amount of the current frame is classified as class "8", the k-space data of the current frame is stored in the FIFO buffer B8. The processing circuitry 51 selects the current frame as the processing target frame, and selects a reference frame from among the other frames stored in the FIFO buffer B8. For example, as the reference frame, a frame stored one frame before the current frame may be selected, or an earliest frame may be selected from among the frames stored in the FIFO buffer B8. Alternatively, a frame with the highest similarity may be selected as the reference frame from among the frames stored in the FIFO buffer B8.

In the case where k-space data of a sufficient number of frames is not accumulated in the FIFO buffer Bn, the processing circuitry 51 may select a reference frame from the frames stored in the FIFO buffer Bn of a close class.

In the above manner, according to modified example 2, the FIFO buffer Bn is provided for each class of the time phase feature amount. The frame stored in the FIFO buffer Bn of the same class as the processing target frame will be highly similar to the processing target frame. Therefore, a reference frame that is highly similar to the processing target frame can be selected without calculating the similarity.

MODIFIED EXAMPLE 3

Processing circuitry 51 according to modified example 3 calculates similarity using a machine learning model in a frame selection function 513.

Figure 7:
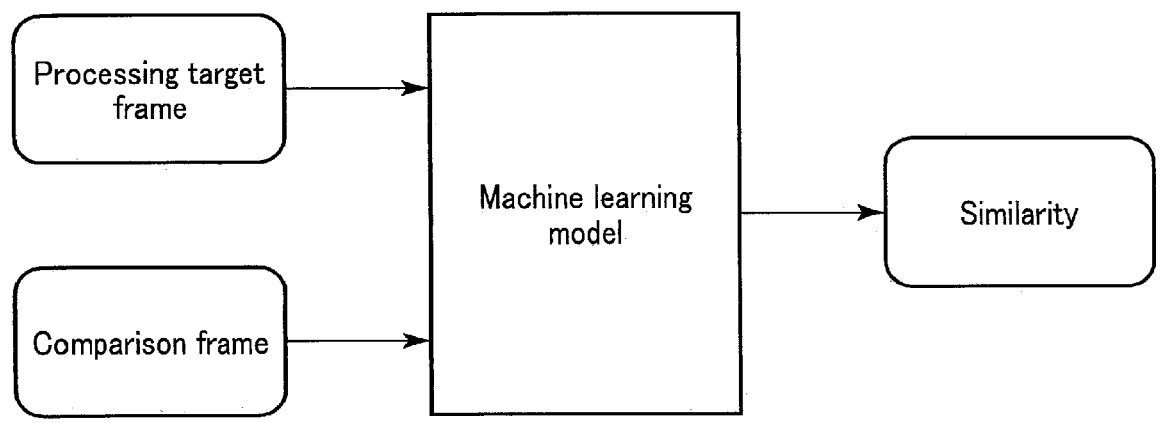
FIG. 7 is a drawing showing an input/output relationship of a machine learning model for a similarity calculation according to modified example 3.

FIG. 7 is a drawing showing an input/output relationship of a machine learning model for a similarity calculation. As shown in FIG. 7, the machine learning model learns parameters so that a time phase feature amount of a processing target frame and a time phase feature amount of a comparison frame are input, and the similarity of signal data of the comparison frame with respect to signal data of the processing target frame is output. The comparison frame indicates a frame to be calculated on the similarity. For example, in the case where the time phase feature amount is k-space data, by applying k-space data of the processing target frame and k-space data of the comparison frame to the machine learning model, the processing circuitry 51 can calculate similarity of the comparison frame with respect to the processing target frame.

According to at least one of the above-explained embodiments, it is possible to improve output accuracy of machine learning.

The term "processor" used in the above explanation indicates, for example, a circuit, such as a CPU, a GPU, or an Application Specific Integrated Circuit (ASIC), and a programmable logic device (for example, a Simple Programmable Logic Device (SPLD), a Complex Programmable Logic Device (CPLD), and a Field Programmable Gate Array (FPGA)). The processor realizes the function by reading and executing the program and the machine learning model stored in the memory circuitry. Instead of storing the program in the memory circuitry, the program and the machine learning model may be directly embedded in the circuit of the processor. In this case, the processor realizes the function by reading and executing the program and the machine learning model embedded in the circuit. The functions corresponding to the program and the machine learning model may also be realized by a combination of logic circuits, and not by executing the program and the machine learning model. Each processor of the present embodiment is not limited to a case of being configured as a single circuit. Therefore, a plurality of independent circuits may be combined to configure a processor, and may realize the function thereof. Furthermore, a plurality of constituent elements shown in FIG. 1 may be integrated into a processor to realize the function thereof.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A signal data processing apparatus comprising processing circuitry,
the processing circuitry comprising:
obtaining first signal data of a plurality of frames that are in time series;
selecting a processing target frame and a reference frame that is similar to the processing target frame from among the plurality of frames; and
inputting first signal data of the processing target frame and first signal data of the reference frame to a machine learning model, and outputting second signal data in which a deficient part of the first signal data corresponding to the processing target frame is reduced.

2. The signal data processing apparatus according to claim 1, wherein the processing circuitry is configured to select, as the reference frame, a frame that satisfies a predetermined criterion of similarity with respect to the processing target frame.

3. The signal data processing apparatus according to claim 1, wherein the processing circuitry is configured to:
   calculate a difference value of a feature amount of first signal data between the processing target frame and each other frame that is different from the processing target frame; and
   select a frame in which the difference value is below a threshold as the reference frame.

4. The signal data processing apparatus according to claim 1, wherein the processing circuitry is configured to:
   obtain output value data of measuring equipment that measures body motion of a subject regarding each of the plurality of frames;
   calculate a difference value of a feature amount of the output value data of the measuring equipment between the processing target frame and each other frame that is different from the processing target frame; and
   select a frame in which the difference value is below a threshold as the reference frame.

5. The signal data processing apparatus according to claim 1, further comprising a buffer that stores the obtained first signal data in order for each frame, wherein the processing circuitry is configured to select first signal data of the reference frame from among the first signal data stored in the buffer.

6. The signal data processing apparatus according to claim 1, further comprising a plurality of buffers that are classified in accordance with a value of a feature amount of the plurality of frames, wherein the processing circuitry is configured to:
   store first signal data of each of the plurality of frames in a buffer to which the feature amount of the frame corresponds among the plurality of buffers; and
   select the reference frame from among the frames stored in a buffer that matches a buffer in which the processing target frame is stored.

7. The signal data processing apparatus according to claim 1, wherein the first signal data is medical signal data acquired by a medical image diagnostic apparatus.

8. The signal data processing apparatus according to claim 1, wherein
   the first signal data includes first k-space data that is acquired by a magnetic resonance imaging apparatus, and a first image based on the first k-space data, and
   the processing circuitry selects as the reference frame other frames in which the first image is similar to the processing target frame.

9. The signal data processing apparatus according to claim 8, wherein the processing circuitry is configured to:
   input the first k-space data or the first image of the processing target frame, and the first k-space data or the first image of the reference frame to the machine learning model, and output second k-space data or a second image of the processing target frame; or
   input the first k-space data of the processing target frame and the first k-space data of the reference frame to the machine learning model, and output the second image of the processing target frame.

10. The signal data processing apparatus according to claim 1, wherein the processing circuitry is configured to input the first signal data of the processing target frame, the first signal data of the reference frame, and similarity of the reference frame with respect to the processing target frame to the machine learning model, and output second signal data of the processing target frame.

11. The signal data processing apparatus according claim 1, wherein the processing circuitry is configured to input the first signal data of the processing target frame, the first signal data of the reference frame, and an acquisition time difference between the processing target frame and the reference frame to the machine learning model, and output second signal data of the processing target frame.

* * * * *